United States Patent
Mullinger et al.

(10) Patent No.: US 8,181,644 B2
(45) Date of Patent: May 22, 2012

(54) INHALATION DEVICE

(75) Inventors: Bernhard Mullinger, Munich (DE); Manuel Frey, Germering (DE); Tobias Kolb, Munich (DE); Tobias Hoffmann, Munich (DE)

(73) Assignee: Activaero GmbH, Gemunden (DE)

( * ) Notice: Subject to any disclaimer, the term of this patent is extended or adjusted under 35 U.S.C. 154(b) by 860 days.

(21) Appl. No.: 12/204,037

(22) Filed: Sep. 4, 2008

(65) Prior Publication Data

US 2009/0064995 A1 Mar. 12, 2009

(30) Foreign Application Priority Data

Sep. 6, 2007 (EP) .................................... 07115812

(51) Int. Cl.
*A61M 15/00* (2006.01)
*A61M 16/00* (2006.01)
*A61M 16/10* (2006.01)
*A62B 7/00* (2006.01)
*A62B 9/00* (2006.01)
*G05B 1/00* (2006.01)

(52) U.S. Cl. ......... 128/203.12; 128/203.14; 128/204.25; 128/205.11

(58) Field of Classification Search . 128/200.14–200.23, 203.12, 203.14–203.15, 128/203.19, 203.21, 203.25, 204.18, 204.25, 128/205.11; *A61M 15/00, 16/00; A62B 7/00, A62B 9/00; G05B 1/00*
See application file for complete search history.

(56) References Cited

U.S. PATENT DOCUMENTS

| | | | | |
|---|---|---|---|---|
| 3,817,246 A | * | 6/1974 | Weigl | 128/204.24 |
| 3,842,828 A | | 10/1974 | Bird | |
| 3,916,888 A | * | 11/1975 | Buck et al. | 128/204.21 |
| 5,007,420 A | * | 4/1991 | Bird | 128/200.14 |
| 5,237,987 A | | 8/1993 | Anderson et al. | |
| 5,666,946 A | * | 9/1997 | Langenback | 128/200.16 |
| 6,405,944 B1 | * | 6/2002 | Benalikhoudja | 239/338 |
| 2005/0061318 A1 | * | 3/2005 | Faram | 128/204.18 |
| 2005/0087189 A1 | * | 4/2005 | Crockford et al. | 128/203.15 |
| 2006/0283447 A1 | * | 12/2006 | Dhuper et al. | 128/203.12 |
| 2007/0023036 A1 | * | 2/2007 | Grychowski et al. | 128/200.14 |
| 2008/0066754 A1 | * | 3/2008 | Faram | 128/204.25 |
| 2010/0043790 A1 | * | 2/2010 | Tatarek | 128/203.14 |

FOREIGN PATENT DOCUMENTS

| | | |
|---|---|---|
| DE | 19939417 | 3/2001 |
| EP | 1700614 | 9/2006 |
| WO | 2004105846 | 12/2004 |
| WO | 2006075184 | 7/2006 |

OTHER PUBLICATIONS

Definition of "along", http://dictionary.reference.com/browse/along.*
European Search Report and Written Opinion from application No. 07115812.5-1257, dated Feb. 2, 2008, 8 pp.

* cited by examiner

*Primary Examiner* — Oren Ginsberg
(74) *Attorney, Agent, or Firm* — Kagan Binder, PLLC

(57) ABSTRACT

The present invention relates to a device for providing an aerosol flow, an air flow or both with at least a compressor for providing an air flow, a nebulization device for generating an aerosol flow and a mixing means for optionally mixing the aerosol flow with the air flow to provide a total flow, wherein the total flow is composed of the aerosol flow, the air flow or both. Further, the device comprises at least a first air channel between the compressor and the nebulization device, at least a second air channel between the compressor and the mixing means and an amplification means for increasing the air flow provided by the compressor.

17 Claims, 7 Drawing Sheets

INHALATION DEVICE

CROSS-REFERENCE TO RELATED APPLICATION

This application claims priority to European Application No. 07115812.5, filed Sep. 6, 2007 and entitled INHALATION DEVICE, which is incorporated herein by reference in its entirety.

TECHNICAL FIELD

The invention relates to a device for providing an aerosol flow and/or an air flow and in particular an inhalation device.

BACKGROUND

Inhalation, i.e., the therapeutic inhalation of aerosol, turned out to be an effective and gentle method for the treatment of various respiratory diseases such as for example acute respiratory disease, chronic obstructive pulmonary disease, and in particular bronchial asthma. Moisturizing the mucous membranes with an aerosol of fine droplets causes dissolving of the mucus in the airways and thereby facilitates the coughing up secretion. Additionally inhaled pharmaceuticals can be applied systematically into the bronchi or the lung where they are effective for the treatment of a topical or systemic disease. Conventionally a nozzle nebulizer is used to provide the aerosol, the nebulizer atomising the active pharmaceutical ingredient using a compressor and a nebulizing nozzle. The penetration depth of the atomized droplets into the lung depends, i.e., on the size of the droplets. Moreover, the specific effect of the droplets can be controlled in that nebulization is only performed during the inhalation process for a certain period of time.

Thus, inhalation devices where the nebulization process can be controlled, depending on the inhalation or exhalation phase, have been reported. German Patent No. 199 39 417 A1, e.g., describes an inhalation device with a control means in which a pneumatic valve is controllable depending on an inhalation phase, an exhalation phase and a rest period. These phases can be determined by a pressure sensor. A further automated inhalation device is described in EP 1 700 614 A1. This document describes a control means which controls an air pump via voltage and/or pulse width modulation to supply an inhalation flow and/or an inhalation volume according to a predetermined chronological sequence to a nebulizer connected to the air pump.

Generally it is desirable that inhalation devices are as small as possible since chronically ill patients, in particular, often carry these devices around. The size and weight of such devices are often predetermined by the compressor. On the one hand, the compressor must generate a sufficiently high enough pressure in order to operate the nebulizing nozzle and on the other hand must provide a sufficiently high air flow to meet the breathing volume per minute of the patient. High pressure and high flows at the same time, however, require a high-performance compressor, which may be accordingly voluminous and heavy.

Thus, it is an object of the present invention to provide an improved device for providing an aerosol flow and/or an air flow. This object is achieved with the features of the claims.

SUMMARY

The present invention provides a maximum air flow with a compressor as small as possible. Accordingly, the present invention relates to a device for providing an aerosol flow and/or an air flow with at least a compressor for providing an air flow, a nebulization device for generating an aerosol flow and a mixing means for optionally mixing the aerosol flow with the air flow to a total flow, wherein the total flow is composed of the aerosol flow and/or the air flow. Furthermore, the device comprises at least a first air channel between the compressor and the nebulization device, at least a second air channel between the compressor and the mixing means and at least an amplification means for increasing the air flow provided by the compressor.

According to a further aspect of the invention, the device has, in addition to or instead of the amplification means, a bypass channel, which connects the first and the second air channel and is suitable for redirecting the air flow in the first air channel into the mixing means via bypassing the nebulization device. This bypass channel can preferably be activated or deactivated by a valve at certain intervals, wherein a constant total flow is maintained.

In a preferred embodiment of the invention, the amplification means has at least one Venturi nozzle. This Venturi nozzle is preferably arranged along the second air channel and suitable for sucking ambient air into the second air channel, preferably via a filter. The Venturi nozzle can be operated at a working pressure between 0.5 and 5 bar, preferably between 0.8 and 3 bar and particularly preferably at 1.2 to 2 bar. The thus created air flow is in a range of 1 to 60 litres per minute. The compressor and the Venturi nozzle are preferably designed such that no pressure and/or flow control is necessary.

In a further preferred embodiment, two or more amplification means are provided. Alternatively, the amplification means may comprise two or more Venturi nozzles preferably connected in series. Thus, it is to be particularly ensured that a sufficient flow is obtained when the nebulization device is not active. The advantage of the Venturi nozzles connected in series is particularly apparent in small inner diameters of the tubes and tubes having a length of more than 1 m. Tubes having a small diameter and a length of more than 1 m facilitate the handling of the hand-held nebulizer. Tubes as used in respirators are not accepted by the patients and increase the contamination risk since aerosol droplets reach the air supply more easily due to the big diameters. In the present invention a tube having a length of 0.2 m to 2 m and an inner diameter of 1 to 20 mm can be used, preferably a tube diameter having an inner diameter of 2 to 5 mm and a length of 0.5 to 1.5 m is used. The Venturi nozzles are dimensioned such that for a precisely specified tube system with known flow resistance upon activated and deactivated nebulizer there is exactly the same inspiration flow at the mouthpiece without the necessity of the device to readjust.

The device further preferably comprises a control means which can vary or determine the aerosol flow and/or the air flow. According to the invention, the total flow of aerosol and/or air flow is to remain basically temporally constant. Total flow is in a range between 1 and 60 litres per minute, preferably between 3 and 50 litres per minute. The nebulization device is suitable for generating an aerosol flow of 1 to 20 litres per minute, preferably 3 to 7 litres per minute and particularly preferably about 6 litres per minute.

Moreover, the device optionally comprises at least a check valve in the second air channel. Further, a bleed valve is added between compressor and nebulization device. Instead of a control via a vent valve, the compressor can be switched on or off.

It is also possible to provide the mixing means as mouthpiece to enable the use of the device as inhalation device.

BRIEF DESCRIPTION OF THE DRAWINGS

Preferred embodiments of the device according to the invention are exemplarily described with reference to the Figures.

DETAILED DESCRIPTION

Figure 1:
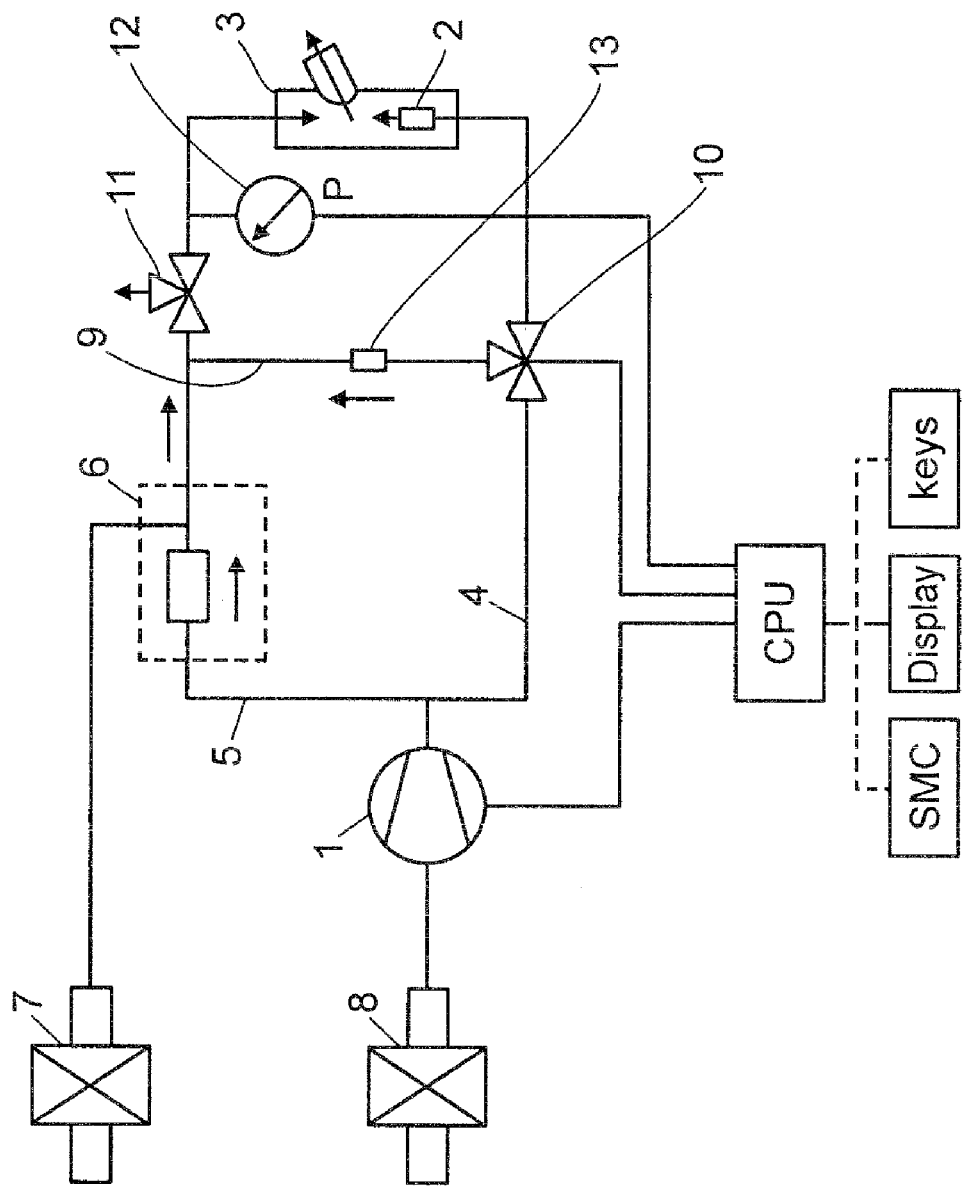
FIG. 1 is a schematic diagram of a preferred embodiment of the inhalation device according to the invention.

FIG. 1 schematically shows a preferred embodiment of the device according to the invention for providing an aerosol flow and/or an air flow. The device comprises a compressor 1 for providing an air flow as well as a nebulization device 2 for generating an aerosol flow. The compressor 1 and the nebulization device 2 are connected to each other via a first air channel 4. The device further comprises a mixing means 3 for optionally mixing the aerosol flow with the air flow to a total flow. In the preferred embodiment, the nebulization device 2 and the mixing means 3 are integrated in one component. However, it is also conceivable that the two means are provided separately and that they are connected to each other via an air channel. In order to use the device as inhalation device, the mixing means is provided with a mouthpiece in the embodiment shown.

The mixing means 3 is connected to the compressor 1 via a second air channel 5. Thus, the air flow generated by the compressor 1 is divided into two partial flows passing through the two air channels 4 and 5. In the second air channel 5, a Venturi nozzle 6 is provided as amplification means, which serves to increase the air flow generated by the compressor 1. The Venturi nozzle 6 sucks additional air through the filter 7 which is then passed on through the second air channel 5 to the mixing means 3. As an alternative to the embodiment shown in FIG. 1, two or more Venturi nozzles 6 can be provided, which are preferably arranged in series to further amplify the generated air flow.

The inlet opening for the compressor 1, too, comprises an air filter 8. The use of a Venturi nozzle is advantageous since a separate pressure relief valve is not necessary anymore then. The Venturi nozzle replaces the pressure relief valve by an appropriate geometry choice. Furthermore, the inhalation flow is independent of the nebulizer geometry. If, e.g., the nebulizing nozzle is too small (e.g., upon an exchange of the nebulizers), the flow via the nebulizer is getting less. However, this is automatically offset in that the flow generated by the compressor flows via the Venturi nozzle to a greater extent. The compressor is designed such that together with the Venturi nozzle and the nebulizing nozzle, an ideal working point is achieved and no control is necessary anymore. The corresponding pressure ratios are set by the geometrical ratios of the nozzles. According to the invention, the inhalation flow is always the same, only the inhalation volume is adjusted according to the patient.

The design shown in FIG. 1 at the same time enables the generation of a sufficiently high pressure to atomize a corresponding active pharmaceutical ingredient in the nebulization device 2 by means of a nebulizing nozzle in order to maintain a sufficiently high air flow which is adapted to the breathing volume per minute of the patient. Here the compressor 1 provides the required pressure and the Venturi nozzle 6 the sufficient flow volume. This embodiment of the inhalation device also involves the great advantage that a compressor can be used which is designed smaller in view of its performance than would actually be necessary for generating the desired pressures and flows. Thus, the invention enables a deliberate undersizing of the compressor which saves costs and space in the housing of the inhalation device.

According to the invention, the preferred device shown in FIG. 1 further comprises a bypass channel 9 which can be activated or deactivated by means of a bypass valve 10. The bypass channel serves to bypass the nebulization device 2. It is the basic idea of the bypass channel 9 to provide a constant total flow, wherein the nebulization can be activated or deactivated. As explained further above, it can be advantageous to carry out the nebulization only at times during the inhalation process. Thus, it is possible to check in which area of the bronchi or the lungs the active aerosol is to be administered. If, however, the nebulization is interrupted during the inhalation process, i.e., no air flows through the first air channel 4 anymore, the patient is not to face a reduced air flow. This problem is solved by the invention in that the bypass valve 10 is switched such that when the nebulization device 2 is deactivated the air flowing through the first air channel 4 is redirected into the bypass channel 9 and the second air channel 5. Thus, the total air flow generated by the compressor 1 is further on administered into the mixing means and thus to the patient. If, on the other hand, the patient does not need the entire air flow provided by the system, e.g., during an inhalation pause, excessive air may be emitted through the valve 11. Alternatively, the compressor 1 can be simply activated or deactivated to control the air flow.

The control or regulation of the valves 10 and 11 as well as the nebulization device 2 is carried out via a control means or CPU, which detects the respective phase of the breathing cycle via a pressure sensor 12 and accordingly switches the valves and the nebulization device. The control means preferably further comprises a display as well as keys for the user to enter information.

Although in the depicted embodiment of the inhalation device both the Venturi nozzle 6 and the bypass channel 9 are displayed, embodiments only comprising the Venturi nozzle 6 or only the bypass channel 9 are also conceivable. Both features individually lead to the fact that a compressor 1 of lower performance can be used. In combination an accordingly stronger effect can be achieved.

FIG. 2*a* shows a circuit diagram of the device according to FIG. 1 and the switching condition of the valves 10 and 11 as well as the air flows occurring during inhalation when the nebulizer is activated. Here the valve 10 is connected such that the compressor 1 is connected to the nebulization device 2 and blocks the bypass channel 9. The valve 11 is connected such at the same time that the compressor is connected to the mixing means 3. This results in the air paths illustrated by the arrows. Accordingly air flows through the filters 7 and 8 into the Venturi nozzle and the compressor and is supplied to the patient via the nebulization device 2 and the mixing means 3. The bypass channel 9 is not used in this context. For example there is a flow of 6 l/m via the first air channel and a flow of 2.8 l/min at, e.g., 1.6 bar via the Venturi nozzle. The flow is increased to 9 l/min through the Venturi nozzle so that all in all the patient is supplied with 15 l/min via the nebulizer mouthpiece. The maximum operation pressure is set via the Venturi nozzle geometry. During an inhalation pause, the bypass channel would be activated so that the flow of 6 l/min would be redirected via the bypass channel to the second air channel 5 and still altogether 15 l/min would flow to the patient.

Figure 2A:
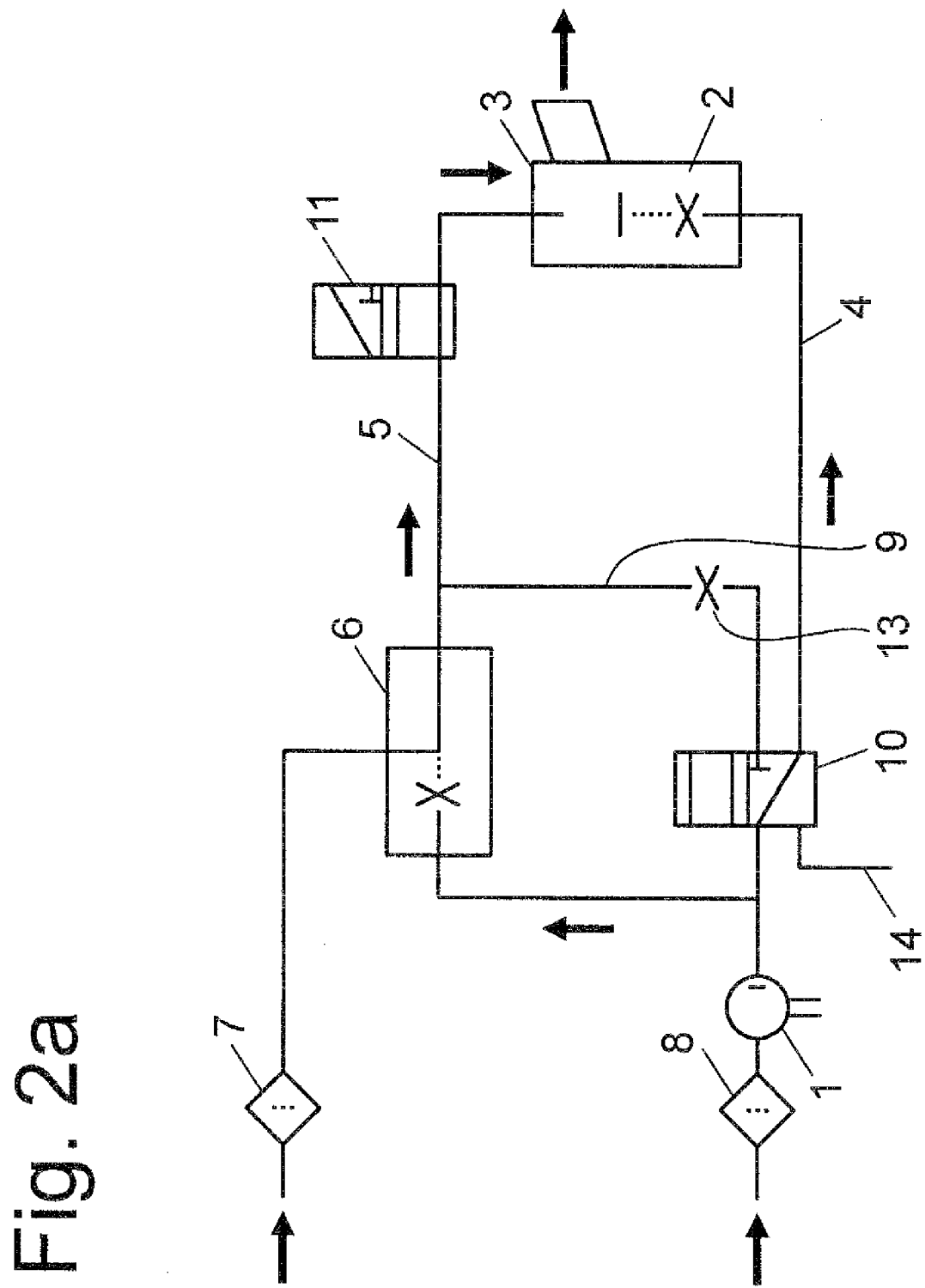
FIG. 2a is a circuit diagram of the device according to FIG. 1 with the air flows occurring during the inhalation upon activated nebuliser.
Figure 2B:
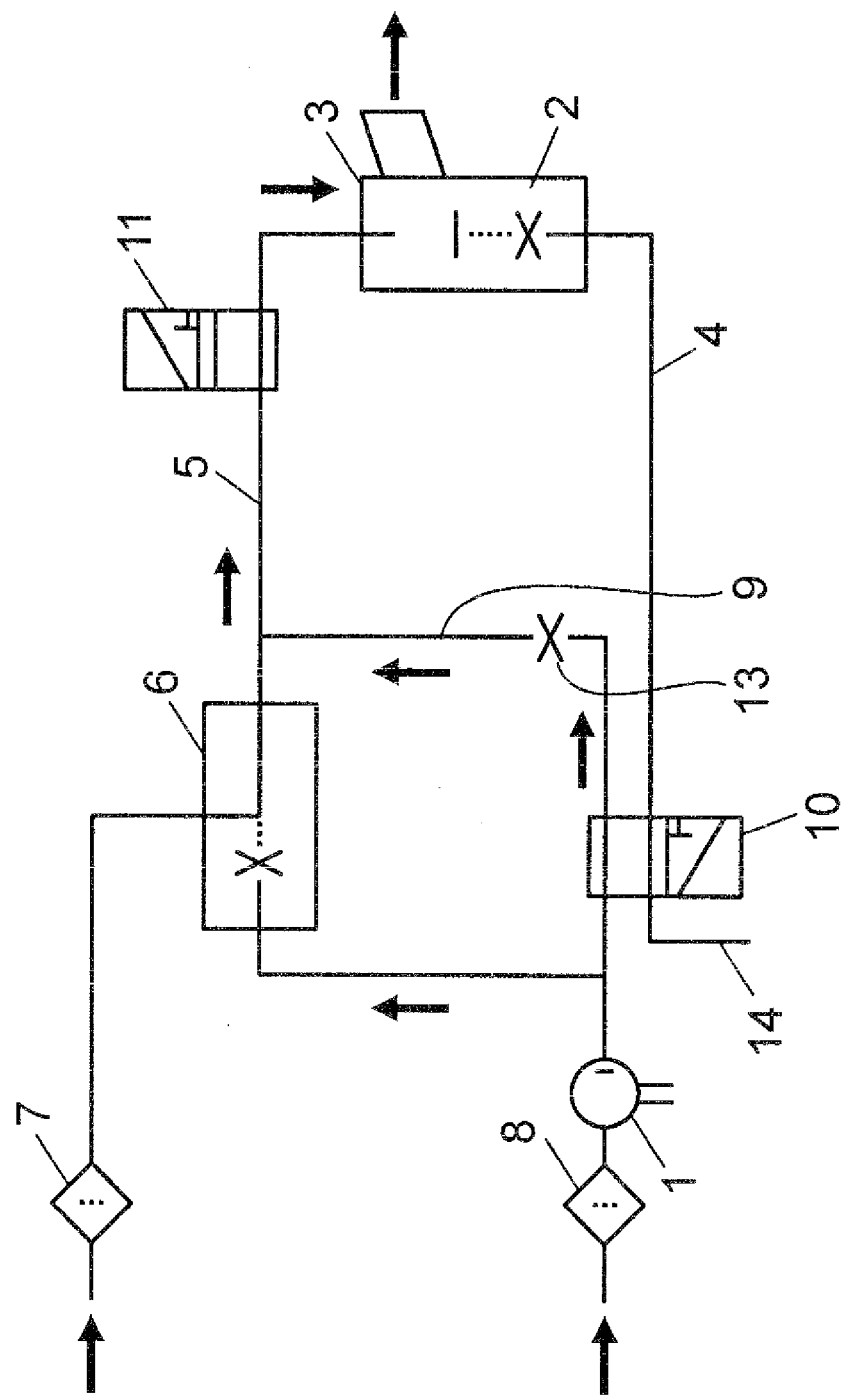
FIG. 2b is a circuit diagram of the device according to FIG. 1 with the air flows occurring during the inhalation upon deactivated nebuliser.

FIG. 2*b* shows a corresponding circuit diagram for inhalation when the nebulization device is deactivated. While the valve 11 is connected like in the circuit of FIG. 2*a*, the valve 10 is a passage for the bypass channel 9. According to the arrows, the air provided by the compressor is now conveyed via the bypass channel 9 and the air channel 5 into the mixing means 3 and provided to the patient exclusively by the latter. The nebulization device is inactive. In order to maintain a constant total flow the air flow passed through the bypass channel 9 is conveyed through a replacement nozzle 13 having the same properties as the nebulizing nozzle in the nebulization device 2. At the same time the depicted position of the valve 10 enables an immediate ventilation of the nebulization device 2 via a vent duct 14. Thus, it is prevented that a remaining pressure in the air channel 4 may cause a further nebulization of the active ingredient.

Figure 2C:
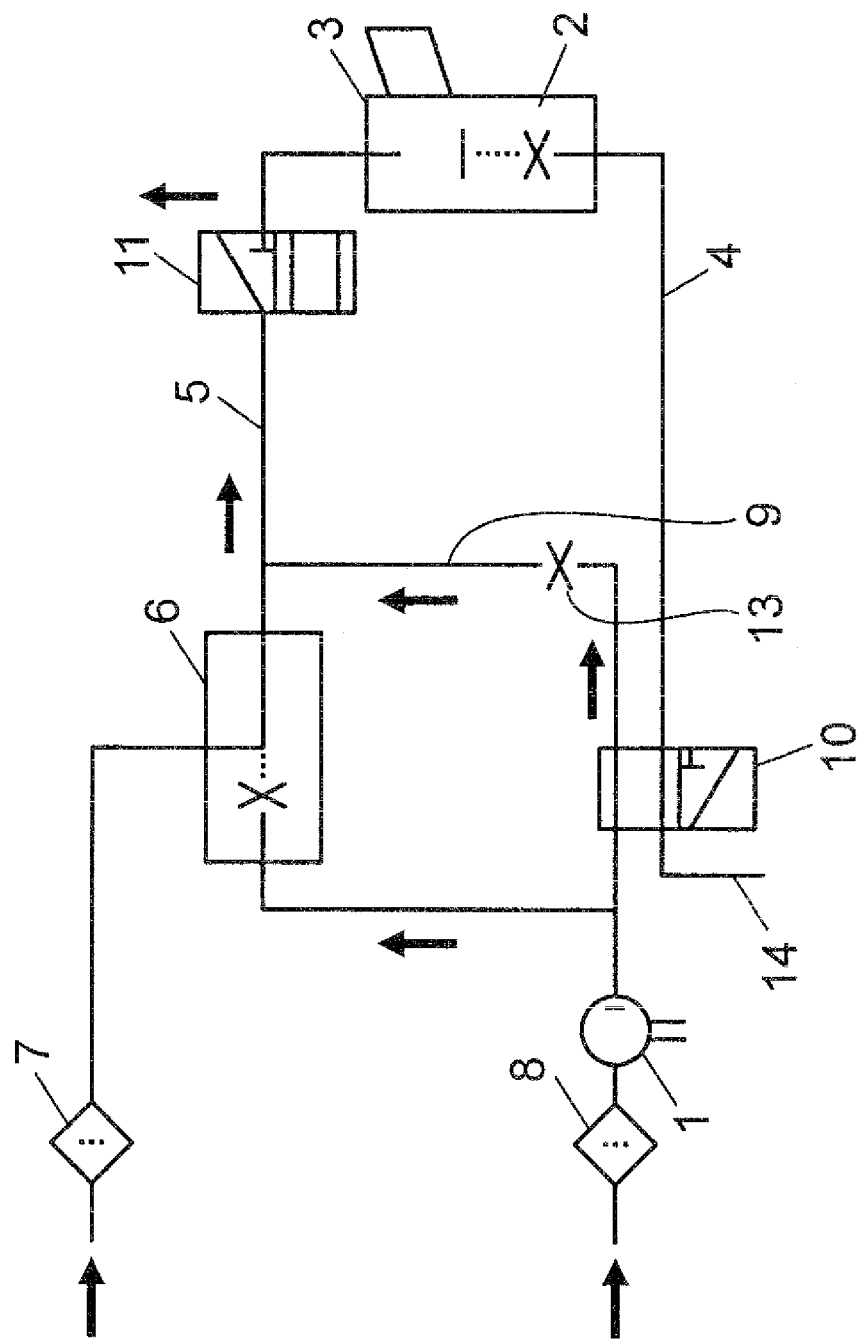
FIG. 2c is a circuit diagram of the device according to FIG. 1 with the air flows occurring during exhalation.

FIG. 2*c* shows a corresponding circuit diagram for exhalation. Again, the corresponding air flows are depicted by arrows. The position of the valve 10 corresponds to that of FIG. 2*b*. However, the valve 11 is switched such that the air supplied by the compressor may escape completely through a vent. At the same time the connection between the Venturi nozzle or the compressor and the mixing means 3 is interrupted such that exhaling into the device is prevented.

Figure 3:
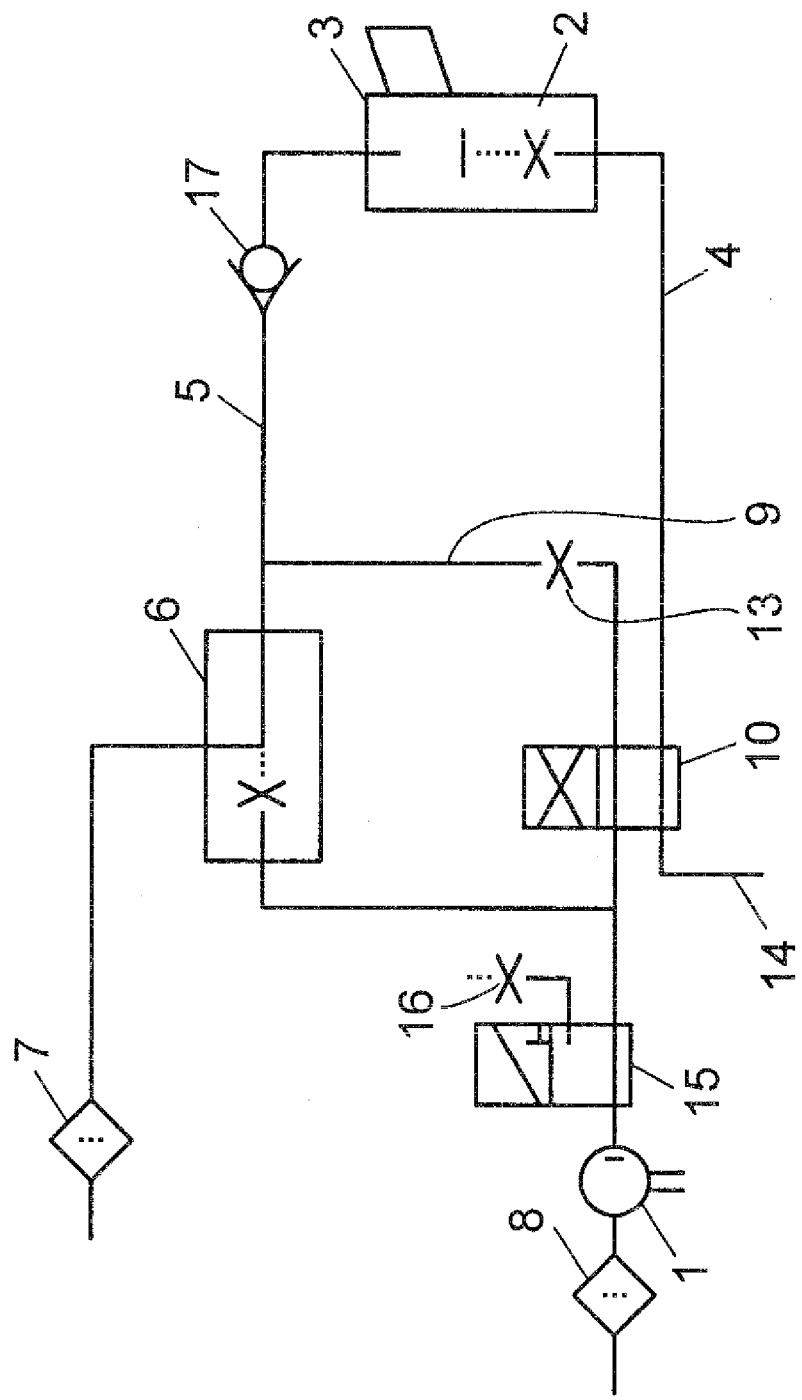
FIG. 3 is a schematic diagram of a further embodiment of the inhalation device according to the invention.
Figure 4:
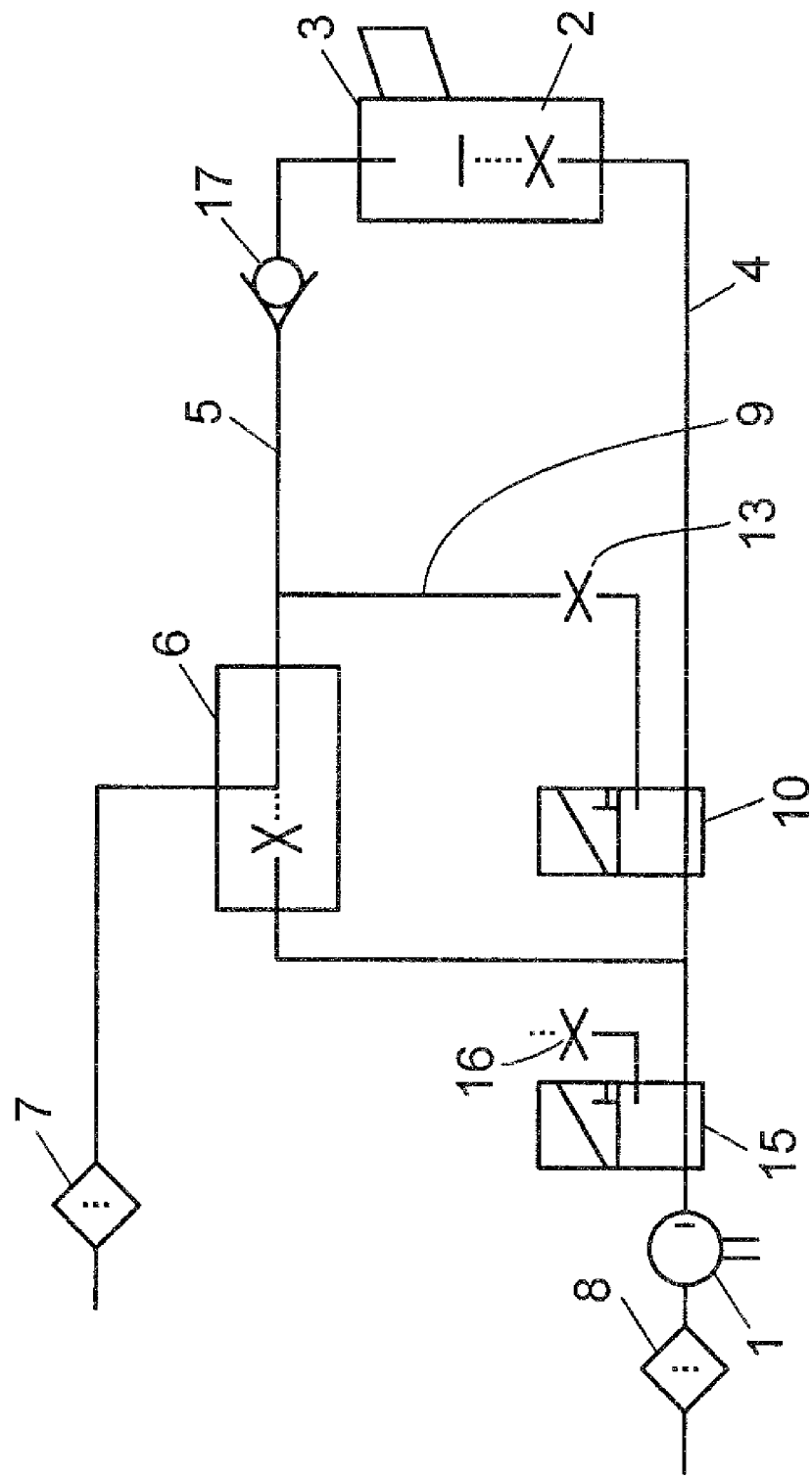
FIG. 4 is a schematic diagram of a further embodiment of the inhalation device according to the invention.
Figure 5:
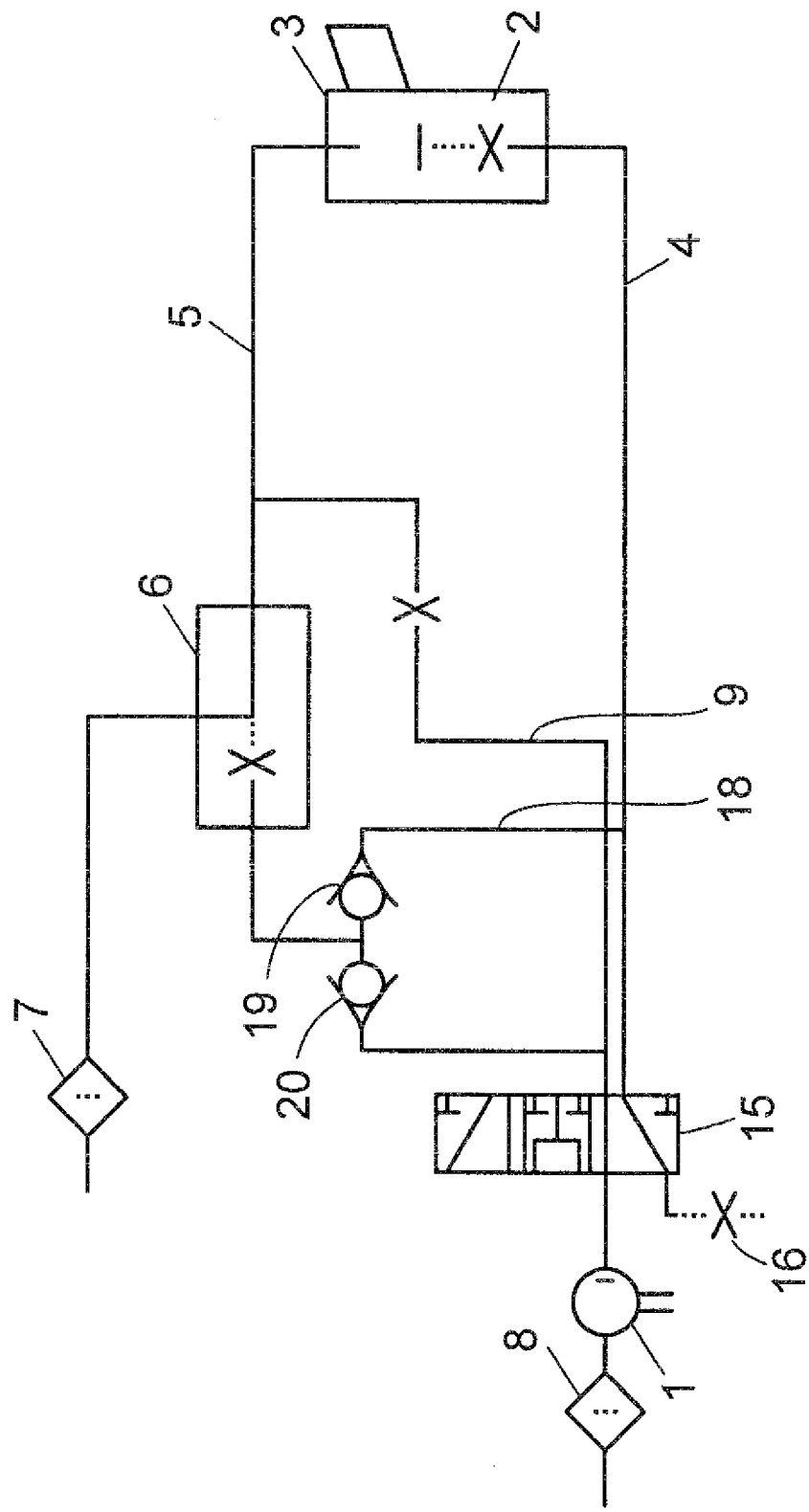
FIG. 5 is a schematic diagram of a further embodiment of the inhalation device according to the invention.

FIG. 3 shows an alternative embodiment of the device according to the invention, wherein the 3/2 valve as shown in FIG. 2 is replaced by a 4/2 valve. Thus, the nebulizer can be immediately switched so as not to exert any pressure upon switch-over to the bypass. Furthermore, the valve 11 has been replaced by a check valve 17 and an additional valve 15 is provided directly behind the compressor 1 with a vent duct 16. During the exhalation process the check valve 17 prevents exhaling into the device, e.g., by a silicone membrane. In this phase of the breathing cycle the compressor 1 is ventilated via the vent duct 16, wherein a nozzle is built therein to maintain the operating pressure of the compressor.

FIG. 4 shows a further embodiment of the invention, wherein no ventilation of the nebulizing nozzle is provided. As mentioned above, this means a delayed deactivation of the aerosol generation whereby the administering of the pharmaceutical can be controlled less precisely. Such an embodiment, however, can nevertheless be taken into consideration due to the costs.

A particularly elegant embodiment using only one valve 15 is shown in FIG. 5. The ventilation of both the nebulization device and the entire system during exhalation can be effected by means of a single vent duct 16. However, therefor a three-step 5/3 valve 15 is required. Further an additional air channel 18 and two check valves 19 and 20 have to be added for an appropriate switching.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

The invention claimed is:

1. A device for providing an aerosol flow, an air flow or both comprising:

a) at least a compressor for providing an air flow;

b) a nebulization device for generating an aerosol flow;

c) a mixing means for optionally mixing the aerosol flow with the air flow to provide a total flow, wherein the total flow comprises the aerosol flow, air flow or both;

d) at least a first air channel arranged between the compressor and the nebulization device;

e) at least a second air channel arranged between the compressor and the mixing means;

f) at least an amplification device for increasing the air flow provided by the compressor, and g) a bypass channel connecting the first and the second air channel and suitable for redirecting the air flow in the first air channel into the mixing means by bypassing the nebulization device.

2. The device according to claim 1, wherein the amplification means comprises at least one or more Venturi nozzles.

3. The device according to claim 2, wherein the Venturi nozzle is arranged along the second air channel and suitable for introducing ambient air into the second air channel via a filter.

4. The device according to claim 2, wherein the Venturi nozzle is operated at 0.5 to 5 bar, at 0.8 to 3 bar, or at 1.2 to 2 bar and provides an air flow of 1 to 60 l/min.

5. The device according to claim 1, further comprising a control means, wherein the aerosol flow, the air flow or both can be varied or determined by the control means.

6. The device according to claim 1, wherein the total flow is substantially temporally constant.

7. The device according to claim 1, further comprising a valve, which enables the activation or deactivation of the bypass channel at certain intervals by maintaining a constant total flow.

8. The device according to claim 1, wherein the compressor and the means for amplification of the air flow are designed such that no pressure and/or flow control is necessary.

9. The device according to claim 1, wherein the nebulization device generates an aerosol flow of 1 to 20 l/min.

10. The device according to claim 1, wherein the nebulization device generates an aerosol flow of 3 to 7 l/min.

11. The device according to claim 1, wherein the nebulization device generates an aerosol flow of 6 l/min.

12. The device according to claim 1, wherein the total flow is in a range between 1 to 60 l/min.

13. The device according to claim 1, wherein the total flow is in a range between 3 to 30 l/min.

14. The device according to claim 1, further comprising at least a check valve in the second air channel.

15. The device according to claim 1, further comprising at least a vent valve between the compressor and nebulization device.

16. The device according to claim 1, wherein the mixing means is configured as a mouthpiece to enable the use of the device as inhalation device.

17. The device according to claim 1, further comprising a tube system for air supply of inhaled air to the nebulizer and having a tube inner diameter of less than 5 mm and a tube length of less than 1.5 m.

* * * * *